US009821019B2

(12) United States Patent
DeMuro

(10) Patent No.: US 9,821,019 B2
(45) Date of Patent: Nov. 21, 2017

(54) COMPOSITIONS AND METHODS FOR TREATMENT OF PAIN

(71) Applicant: Princeton Biotechnology Corporation, Barrington, NJ (US)

(72) Inventor: Frank DeMuro, Barrington, NJ (US)

(73) Assignee: Princeton Biotechnology Corporation, Barrington, NJ (US)

( * ) Notice: Subject to any disclaimer, the term of this patent is extended or adjusted under 35 U.S.C. 154(b) by 0 days.

(21) Appl. No.: 15/005,410

(22) Filed: Jan. 25, 2016

(65) Prior Publication Data

US 2016/0136215 A1 May 19, 2016

Related U.S. Application Data

(63) Continuation of application No. 14/384,823, filed as application No. PCT/US2013/030448 on Mar. 12, 2013, now Pat. No. 9,278,116.

(60) Provisional application No. 61/685,352, filed on Mar. 15, 2012.

(51) Int. Cl.
| | |
|---|---|
| *A61K 36/00* | (2006.01) |
| *A61K 36/28* | (2006.01) |
| *A61K 33/38* | (2006.01) |
| *A61K 36/185* | (2006.01) |
| *A61K 33/04* | (2006.01) |
| *A61K 36/38* | (2006.01) |
| *A61K 9/00* | (2006.01) |
| *A61K 35/74* | (2015.01) |
| *A61K 36/31* | (2006.01) |
| *A61K 31/17* | (2006.01) |
| *A61K 41/00* | (2006.01) |

(52) U.S. Cl.
CPC ............ *A61K 36/28* (2013.01); *A61K 9/0014* (2013.01); *A61K 31/17* (2013.01); *A61K 33/04* (2013.01); *A61K 33/38* (2013.01); *A61K 35/74* (2013.01); *A61K 36/185* (2013.01); *A61K 36/31* (2013.01); *A61K 36/38* (2013.01); *A61K 41/0004* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 5,795,573 A | 8/1998 | Paradise | |
| 5,834,443 A | 11/1998 | Masiello | |
| 6,024,734 A | 2/2000 | Brewitt | |
| 6,039,954 A | 3/2000 | Yu et al. | |
| 6,159,473 A | 12/2000 | Watkins et al. | |

(Continued)

FOREIGN PATENT DOCUMENTS

| | | |
|---|---|---|
| DE | 202010011296 U1 | 11/2010 |
| WO | 9955299 A1 | 11/1999 |

OTHER PUBLICATIONS

Atiyeh et al. "Effect of silver on burn wound infection control and healing: Review of the literature", Burns, (Mar. 2007), vol. 33, pp. 139-148.

(Continued)

*Primary Examiner* — Rosanne Kosson
(74) *Attorney, Agent, or Firm* — Lerner, David, Littenberg, Krumholz & Mentlik, LLP

(57) ABSTRACT

The present invention relates to a homeopathic formulation comprising dilutions of *Arnica, Calendula, Echinacea, Hypericum*, Silver, Sulfur, *Thiosinaminum, Urtica*, and methods for treating pain, inflammation, scar tissue, itching/pruritus and infection using same.

4 Claims, 2 Drawing Sheets

(56) References Cited

U.S. PATENT DOCUMENTS

| | | |
|---|---|---|
| 6,207,163 B1 | 3/2001 | Boublik et al. |
| 6,239,105 B1 | 5/2001 | Brewitt |
| 6,770,263 B1 | 8/2004 | Brucker |
| 7,195,781 B2 | 3/2007 | Miketin |
| 7,229,648 B2 | 6/2007 | Dreyer |
| 7,740,886 B1 | 6/2010 | Vargas |
| 7,871,647 B1 | 1/2011 | Paradise |
| 2009/0214504 A1 | 8/2009 | Carter et al. |
| 2009/0232904 A1 | 9/2009 | Quinto et al. |
| 2009/0280184 A1 | 11/2009 | DeSica et al. |
| 2010/0151052 A1 | 6/2010 | Wycoff |
| 2010/0316737 A1 | 12/2010 | Farrington et al. |
| 2011/0038949 A1 | 2/2011 | Oswal et al. |

OTHER PUBLICATIONS

Chinese Search Report from the First Office Action dated Feb. 28, 2017 in Appln. No. 201380025518.4, English text only; Examiner cannot read Chinese.

International Search Report for Application No. PCT/US2013/030448 dated Jun. 21, 2013.

Atiyeh et al: "Effect of silver on burn wound infection control and healing: Review of the literature", Burns, Butterworth Heinemann, GB, val. 33, No. 2, Feb. 3, 2007 (Feb. 3, 2007), pp. 139-148, XP005873104.

Aabel S et al: "Nuclear magnetic resonance (NMR) studies of homeopathic solutions.", US National Library of Medicine (NLM), Bethesda, MD, US; Jan. 2001 (Jan. 2001 ), XP002751174, Database Medline [Online] US National Library of Medicine (NLM), Bethesda, MD, US; Database accession No. NLM11212083; & The British Homoeopathic Journal Jan. 2001, vol. 90, No. 1, Jan. 2001, pp. 14-20.

Hopff W H: "[History of "special therapeutic directions": the example of homeopathy].", Zeitschrift for Arztliche Fortbildung Apr. 1996, vol. 90, No. 2, Apr. 1996 (Apr. 1996), pp. 91-96, XP009187314 (English Abstract provided).

Haustein K O: "[Homeopathy from the viewpoint of the clinical pharmacologist].", Zeitschrift for Arztliche Fortbildung Apr. 1996, vol. 90, No. 2, Apr. 1996 (Apr. 1996), pp. 97-101, XP009187315 (English Abstract provided).

Jutte et al: "A review of the use and role of low potencies in homeopathy", Complementary Therapies in Medicine, Churchill Livingstone, Edinburgh, GB, vol. 13 , No. 4, Dec. 1, 2005 (Dec. 1, 2005), pp. 291-296, XP005198468.

Extended European Search Report Application No. 137601297.5 dated Dec. 2, 2015.

Jonas, W.B. et al., "A Critical Overview of Homeopathy", Annals of Internal Medicine, Mar. 2003, pp. 393-399, vol. 138, No. 5, American College of Physicians, New York. NY, US.

US 9,821,019 B2

COMPOSITIONS AND METHODS FOR TREATMENT OF PAIN

CROSS-REFERENCE TO RELATED APPLICATIONS

The present application is a continuation of U.S. 14/384,823, filed Sep. 12, 2014, which is a national phase entry under 35 U.S.C. §371 of International Application No. PCT/US2013/030448 filed Mar. 12, 2013, which claims priority to U.S. patent application No. 61/685,352 filed Mar. 15, 2012, all of which are hereby incorporated herein by reference.

BACKGROUND OF THE INVENTION

Historically aches, pains and bodily discomfort have engaged people, as well as their animals and pets, for thousands of years. Yet, when one looks at the pain remediation marketplace of today, it becomes apparent that no one product has as yet been developed that has the ability to offer one hundred percent relief, particularly pain relief to any one individual. As such, people today desiring to reduce or stop their suffering from pain/aches and/or pruritus will often attempt to seek relief from the use of one or more drugs from the category of non-prescription and/or prescription drugs that are in fairly large abundance worldwide, with hundreds from which to choose.

Unfortunately many of these drugs have unwanted side effects that can often compromise health and well-being; they include overdosing, severe allergic and/or hypersensitivity reactions, unsightly rashes, moderate to severe breathing difficulties, suicidal thoughts, blurry vision, gastric upset, and liver dysfunction. These drugs can also cause death, even when drug instructions are followed assiduously. Clearly there is a need for a safer if not a better alternative.

BRIEF SUMMARY OF THE INVENTION

A homeopathic formulation of the present invention comprises at least one dilution of *Arnica*, at least one dilution of *Calendula*, at least one dilution of *Echinacea*, at least one dilution of *Hypericum*, at least one dilution of Silver, at least one dilution of Sulfur, at least one dilution of *Thiosinaminum*, and at least one dilution of *Urtica*. In one embodiment, the dilutions of *Arnica, Calendula, Echinacea, Hypericum*, Silver, Sulfur, *Thiosinaminum*, and *Urtica* include dilutions of C and M potencies. In some embodiments, the C potency of the dilutions of *Arnica, Calendula, Echinacea, Hypericum*, Silver, Sulfur, *Thiosinaminum*, and *Urtica* ranges from about 5 C to about 50 C. In other embodiments, the M potency of the dilutions of *Arnica, Calendula, Echinacea, Hypericum*, Silver, Sulfur, *Thiosinaminum*, and *Urtica* ranges from about 5 M to about 100 M. In various embodiments, the formulation of the present invention further comprises at least one dilutions of Nosode. In some embodiments, the Nosode comprises an infection agent such as one or more selected from the group consisting of Methicillin-resistant *Staphylococcus aureus* (MRSA), microplasms, *Aspergillus niger, Candida, Mucor racemosus*, Gram-negative bacteria, and Gram-positive bacteria. In one embodiment, the formulation further comprises an inactive ingredient.

In some embodiments, the formulation of the present invention can be used to treat pain, inflammation and/or infection. In various embodiments, the formulation of present invention can be sued by applying the topical spray of the formulation of directly onto an area of concern on the outside or inside a patient's body.

DETAILED DESCRIPTION

Figure 1:
FIG. 1 is a photograph of the burn wounds on hand.

The present invention will be described in more detail below.

All percentages and ratios used herein are by weight of the total composition and all measurements made are at about room temperature and normal pressure unless otherwise designated. "Room temperature" as defined herein means a temperature ranging between about 22° C. and about 26° C. All temperatures are in degrees Celsius unless specified otherwise.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

As used herein, "consisting essentially of" means that the invention may include ingredients in addition to those recited in the claim, but only if the additional ingredients do not materially alter the basic and novel characteristics of the claimed invention. Preferably, such additional ingredients will not be present at all or only in trace amounts. However, it may be possible to include up to about 10% by weight of materials that could materially alter the basic and novel characteristics of the invention as long as the utility of the compounds (as opposed to the degree of utility) is maintained.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Note that while the specification and claims may refer to a final product containing a certain reactant or a certain amount, it may be difficult to tell from the product that any particular recitation is satisfied. Such a recitation may be satisfied, however, if the materials used prior to final production, for example, meet that recitation. Indeed, as to any property or characteristic of a final product which cannot be ascertained from the final product directly, it is sufficient if that property resides in the components recited just prior to production steps used to make the composition.

As used herein, a "homeopathic formulation" is defined as a formulation including at least one tincture of a drug labeled as being homeopathic, which is listed in the Homeopathic Pharmacopeia of the United States (HPUS).

Dilution

A homeopathic formulation begins with a mother tincture, which means a remedy (e.g., a medicinal substance or Nosode) to be used dissolved in water or alcohol. The mother tincture can be diluted. For example, if the mother tincture is diluted by 1 part in 100 of water (1:100), it is known as a "C" potency. If another dilution is then done to the 1C dilution, a 2C dilution (1 part mother tincture in 10,000 of water) can be produced. A further 1C dilution of the 2C dilution can produce a 3C dilution (1 part mother tincture in 1,000,000 of water). The iteration can be repeated to produce formulation of differing potency.

If the mother tincture is diluted by 1 part in 10 (1:10), it is known as "X" potency. If the mother tincture is diluted by 1 part in 1000 (1:1000), then it is known as "M" potency. The iteration of 1X and 1M can be repeated, respectively, to produce formulation of differing potency.

Various dilutions can be made from a mother tincture as discussed above. In some embodiments, these dilutions can be blended together to produce a final formulation. For example, a mother tincture of an ingredient 1, $I_1$, can be used to form dilutions of 10C, 30C, and 50M, symbolized by: $I_1 10C$ and $I_1 30C$ and $I_1 50M$, respectively. Then, certain amounts of these different dilutions having different potency can be blended together to produce a final formulation.

Blending

There are numerous strategies/techniques that could be used to blend dilutions together. For example, equal or differing volumes of dilutions could be blended together. In one embodiment, equal volumes of the dilutions of the same ingredient, $I_1$, could be blended together as illustrated in Table 1 below to produce a formulation:

TABLE 1

| Ingredient | Potency | Amount |
|---|---|---|
| $I_1$ | 10C | 1 liter |
|  | 30C | 1 liter |
|  | 50M | 1 liter |
| FINAL FORMULATION |  | 3 liter of $I_1 10C/30C/50M$ |

In other embodiments, a formulation can include blended dilutions of various ingredients by equal or differing volumes of dilutions. Below describes various blending strategies which can be used to produce a final homeopathic formulation in accordance with the present invention.

Some blending strategies can include forming blends, $C_k$, of various ingredients, $I_i$, at specific dilutions, $D_k$, and then further blending the blends, $C_k$, together. For example, a blend of various $C_k$ may described by the Formula I below:

$$\Sigma C_k = \Sigma D_k (\Sigma I_i)$$ Formula I

For example, $C_1 = I_1 10C + I_2 10C + \ldots + I_i 10C$, wherein $D_1 = 10C$;

$C_2 = I_1 30C + I_2 30C + \ldots + I_i 30C$, wherein $D_2 = 30C$; and $C_3 = I_1 50M + I_2 50M + \ldots + I_i 50M$, wherein $D_3 = 50M$.

Yet other blending strategies can be employed, such as producing a blended volume equal to the volume of each starting dilution. For example, in such a strategy, fractional volumes of each dilution can be used to form a blend. Below Table 2 illustrates a non-limiting illustration of such blending strategy:

TABLE 2

| Fractional Volume | Dilution |
|---|---|
| 5/26 | 3 liters of $I_1 10C$ |
| 8/26 | 3 liters of $I_1 30C$ |
| 13/26 | 3 liters of $I_1 50C$ |
| FINAL FORMULATION | 3 liter of $I_1 10C/30C/50C$ |

Similar blends can be made for additional ingredients. The blends of various ingredients can be further mixed together. Thus, many blending strategies can be utilized to produce the product herein taught.

Other blending strategies are possible, such as any of those that utilize aspects of mathematics, harmonic ordering, quantum resonance, probabilities, weighted averages, or other various mathematical and/or scientific theories and/or formalisms.

Succussion

In some embodiments, a diluted formulation of a mother tincture, for example, as discussed above, can be agitated by a process known as "succussion". Succussion may include shaking a formulation vigorously, staccato stirring, or otherwise agitating the formulation or blend in a suitable container/vessel, such as one made from PET, glass, or stainless steel. Succussion techniques can employ either or both of those of Hahnemann and Korsakov, and can be performed by hand and/or with suitable equipment, such as those from LABOTICS, such as a Dynamat, Impregmat or K-Tronic. Succussion can improve retention of the properties of the mother tincture in the dilution. One or more succussion techniques can be performed at any stage or iteration of the manufacturing process, for example, on one or more dilutions prior to blending those dilutions, or on the blended product of those dilutions, or on some dilutions but not other dilutions, or the like. The same or different succussion techniques can be applied to each dilution or blend at any stage of the manufacturing process.

One or more succussions can be performed during one or more iterations, each iteration occurring for a time interval. The number of successions that can be performed during each iteration can range from about 10 to about 1000, preferably about 15 to about 150. The time interval of each iteration may be constant or variable. In some embodiments, the time interval of each iteration may range from about 6 seconds to about 150 seconds, preferably about 20 seconds to about 40 seconds.

In some embodiments, a number of succussions per iteration can be patterned to a mathematical series, S, such as a Fibonacci series or any suitable series, with a harmonic multiplier, H, as described by the Formula II below:

$$\sum_{i=a}^{k} (S_i) H \Big|_V^{T_{function}} = U$$ Formula II

The harmonic multiplier can be constant or variable, such as dependent on a mathematical function. For example, "k" iterative succussions can be performed to a volume, V, within a constant time interval using a Fibonacci Series, S=1, 1, 2, 3, 5, 8, 13, 21, 34, 55 . . . n, modified by a harmonic multiplier, H, which is a constant and equal to 10 in this example. Using the exemplary succussion pattern described above of Formula II, this Volume, V, would experience the sum total of succussions, U, where U=1430 succussions as shown by Table 3 below.

TABLE 3

| Iteration | Number of Succussions | Time Interval (min) |
|---|---|---|
| 1 | 10 | 1 |
| 2 | 10 | 1 |
| 3 | 20 | 1 |
| 4 | 30 | 1 |
| 5 | 50 | 1 |
| 6 | 80 | 1 |
| 7 | 130 | 1 |
| 8 | 210 | 1 |
| 9 | 340 | 1 |
| 10 | 550 | 1 |
| TOTAL SUCCUSSIONS | 1430 | |

Other succussion strategies are possible, such as any of those that utilize aspects of mathematics, harmonic ordering, quantum resonance, probabilities, weighted averages, or other various mathematical and/or scientific theories and/or formalisms.

Arnica

Arnica has been used for medicinal purposes since the 1500s. In general the constituent base is complex, consisting of a wide variety of chemicals of variable effect and potency; for example, one such complex can contain derivatives of thymol also known as 2-isopropyl-5-methylphenol, a naturally occurring biocide with strong antimicrobial/anti-fungal attributes that can reduce bacterial resistance to common drugs such as penicillin. Numerous studies have demonstrated its antimicrobial (including Aeromoans hydrophila and Staphylococcus aureus) effects, ranging from inducing antibiotic susceptibility in drug-resistant pathogens to powerful antioxidant properties, and to reduce bacterial resistance to antibiotics through a synergistic effect; it has also been shown to be effective particularly against Fluconazole-resistant strains, and there is evidence of anti-tumor properties. Arnica can be used to reduce inflammation, to heal wounds, and/or for injuries such as sprains and bruises. Arnica can be used to speed recovery from soreness and bruising associated with surgery. Homeopathic formulations in accordance of the present invention can include tinctures and/or dilutions of Arnica. In some embodiments, a mother tincture of Arnica can include about 1 to about 30 grams of Arnica dissolved in about 30 to about 60 ml of water and/or alcohol. Various dilutions can be made from the mother tincture. Dilutions of Arnica may include X, C and M dilutions. X dilutions may range in potency from about mother tincture to about 500 X; about 2 X to about 300 X; about 5 X to about 100 X; about 5 X to about 50 X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5M to about 100 M. Succussion can be performed on any Arnica dilution, prior to, or after blending to form a homeopathic formulation. In some embodiments, homeopathic formulations can be made from Arnica dilutions of 10C. In other embodiments, homeopathic formulations can be made from Arnica dilutions of 30C. In yet other embodiments, homeopathic formulations can be made from Arnica dilutions of 50M. In another embodiment, homeopathic formulations is a blended formulation including various Arnica dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include Arnica dilutions in an amount ranging from about 5% to about 40%, about 10% to about 20% relative to the total volume of the final formulation.

Calendula

Calendula plant pharmacological studies have suggested that Calendula extracts may have antiviral, antigenotoxic, cytotoxic anti-tumor, anti-inflammatory and lymphocyte activation properties. Users in trials also experienced less radiation induced pain and fewer breaks in treatment. Homeopathic formulations in accordance of the present invention can include tinctures and/or dilutions of Calendula. In some embodiments, a mother tincture of Calendula can include about 1 to about 30 grams of Arnica dissolved in about 30 to about 60 ml of water and/or alcohol. Various dilutions can be made from the mother tincture. Dilutions of Calendula may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any Calendula dilution, prior to, or after blending to form a homeopathic formulation. In some embodiments, homeopathic formations can be made from include Calendula dilutions of 10C. In other embodiments, homeopathic formulations can be made from Calendula dilutions of 30C. In yet other embodiments, homeopathic formulations can be made from Calendula dilutions of 50M, In another embodiment, homeopathic formulations is a blended formulation including various Calendula dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include Calendula dilutions in an amount ranging from about 5% to about 40%, about 10% to about 20% relative to the total volume of the final formulation Echinacea Archaeologists have found evidence that Native Americans may have used Echinacea for more than 400 years to treat infection and wounds. Today's uses include a method to shorten the duration of the common cold and flu and reduce symptoms, such as sore throat/pharyngitis, cough, and fever. Several laboratory and animal studies suggest that it contains active substances that enhance the activity of the immune system, relieve pain, reduce inflammation, and have hormonal, antiviral, and antioxidant effects. Often recommended to treat urinary tract infections, vaginal yeast (Candida) infections, ear infections, athlete's foot, sinusitis, hay fever/allergic rhinitis, as well as slow-healing wounds. The constituent base for echinacea is complex, consisting of a wide variety of chemicals of variable effect and potency. Some chemicals may be directly antimicrobial, while others may work at stimulating or modulating different parts of the immune system. Chemical constituents include phenols (cichoric acid and caftaric acid); others that may have important health effects include alkylamides and polysaccharides. The immunomodulatory effects of echinacea preparations are likely caused by fat-soluble alkylamides (alkamides). Alkylamides bind particularly to human CB2 and to a much lesser degree to CB1 receptors; as a result they are implicated in a variety of modulatory functions, including immune suppression, induction of apoptosis, cell migration and inhibition of tumor necrosis factor α TNF-alpha. Although the triggering factors for many autoimmune diseases are not known, one of the key inflammatory mediators in the attending chronic inflammatory process is the cytokine, tumor necrosis factor-alpha (TNF-α). TNF-α overexpression acts as a driver for inflammation that damages cartilage, bone and bowel mucosa, and TNF-α inhibition leads to significant clinical improvements and reduction of this damage.

Homeopathic formulations in accordance of the present invention can include tinctures and/or dilutions of *Echinacea*. In some embodiments, a mother tincture of *Echinacea* can include about 1 to about 30 grams of *Echinacea* dissolved in about 30 to about 60 ml of water and/or alcohol. Various dilutions can be made from the mother tincture. Dilutions of *Echinacea* may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50 C. M dilutions may range in potency from about mother tincture to about 1000 M; about 2 M to about 300 M; about 5 M to about 200 M; about 5 M to about 100 M. Succussion can be performed on any *Echinacea* dilution, prior to, or after blending to form a homeopathic formulation. In some embodiments, homeopathic formations can be made from include. *Echinacea* dilutions of 10C. In other embodiments, homeopathic formulations can be made from *Echinacea* dilutions of 30C. In yet other embodiments, homeopathic formulations can be made from *Echinacea* dilutions of 50M. In another embodiment, homeopathic formulations is a blended formulation including various *Echinacea* dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include *Echinacea* dilutions in an amount ranging from about 5% to about 40%, about 10% to about 20% relative to the total volume of the final formulation

*Hypericum*

*Hypericum* has a history of being used as a medicine dating back to ancient Greece with antibacterial and antiviral properties. Its anti-inflammatory properties are useful when applied to the skin to help heal not only wounds and burns, but also eczema and hemorrhoids. In recent years it has been studied extensively as a treatment for depression. A number of studies show that it may help treat mild-to-moderate depression. An early study suggests that it may also help relieve physical and emotional symptoms of Premenstrual syndrome/PMS in some women, including cramps, irritability, food cravings, and breast tenderness. It may also help to improve mood and anxiety during menopause.

Homeopathic formulations in accordance of the present invention can include tinctures and/or dilutions of *Hypericum*. In some embodiments, a mother tincture of *Hypericum* can include about 1 to about 30 grams of *Hypericum* dissolved in about 30 to about 60 ml of water and/or alcohol. Various dilutions can be made from the mother tincture. Dilutions of *Hypericum* may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any *Hypericum* dilution, prior to, or after blending to form a homeopathic formulation. In some embodiments, homeopathic formations can be made from include *Hypericum* dilutions of 10C. In other embodiments, homeopathic formulations can be made from *Hypericum* dilutions of 30C. In yet other embodiments, homeopathic formulations can be made from *Hypericum* dilutions of 50M. In another embodiment, homeopathic formulations is a blended formulation including various *Hypericum* dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include *Hypericum* dilutions in an amount ranging from about 5% to about 40%, about 10% to about 20% relative to the total volume of the final formulation

*Thiosinaminum*

*Thiosinaminum* is a trituration of the crystals of allyl sulphocarbamide. Uses include resorbing/dissolving/reduction of scar tissue/fibrosis, tumors, strictures, plantar fasciitis, immune system diseases, enlarged glands, eye concerns, scleroderma, tinnitus aurium, amenorrhea, cystic fibrosis, polycystic ovaries, fibroids and pelvic adhesions. Homeopathic formulations in accordance of the present invention can include tinctures and/or dilutions of *Thiosinaminum*. In some embodiments, a mother tincture of Thiosinaminum can include about 1 to about 30 grams of *Thiosinaminum* dissolved in about 30 to about 60 ml of water and/or alcohol. Various dilutions can be made from the mother tincture. Dilutions of *Thiosinaminum* may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any *Thiosinaminum* dilution, prior to, or after blending to form a homeopathic formulation. In some embodiments, homeopathic formations can be made from include *Thiosinaminum* dilutions of 10C. In other embodiments, homeopathic formulations can be made from *Thiosinaminum*dilutions of 30C. In yet other embodiments, homeopathic formulations can be made from *Thiosinaminum* dilutions of 50M. In another embodiment, homeopathic formulations is a blended formulation including various *Thiosinaminum* dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include *Thiosinaminum* dilutions in an amount ranging from about 5% to about 40%, about 10% to about 20% relative to the total volume of the final formulation.

Silver

Silver has a proven record of broad-spectrum antimicrobial activity that includes antibiotic-resistant bacteria, with minimal toxicity toward mammalian cells at low concentrations, and has a less likely tendency than antibiotics to induce resistance due to its activity at multiple bacterial target sites. Silver combined with sulfur is used to topically treat infections of second- and third-degree burns. Wound dressings that contain silver are increasing in importance due to the recent increase of antibiotic-resistant bacteria, such as MRSA. Homeopathic formulations in accordance of the present invention can include tinctures and/or dilutions of Silver. In some embodiments, a mother tincture of Silver can include about 0.1 to about 3 grams of Silver dissolved in about 30 to about 60 ml of water and/or alcohol. Various dilutions can be made from the mother tincture. Dilutions of Silver may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any Silver dilution, prior to, or after blending to form a homeopathic formulation. In some embodiments, homeopathic formations can be made from include Silver dilutions of 10C. In other embodiments, homeopathic formulations can be made from Silver dilutions of 30C. In yet other embodiments, homeopathic formulations can be made from Silver dilutions of 50M. In another embodiment, homeopathic formulations is a blended formulation including various Silver dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include Silver dilutions in an amount ranging from about 5% to about 40%, about 10% to about 20% relative to the total volume of the final formulation.

In addition to including Silver dilutions in the homeopathic formulation, Silver can be further added to the homeopathic formulation as an inactive ingredient, for example, as a preservative.

Sulfur

Sulfur has been in therapeutic use for over 2,000 years, especially for its antiseptic attributes. Sulfur also helps to control itching/irritation. Sulfur combined with silver is used to topically treat infections of second- and third-degree burns; it also kills a wide variety of bacteria. Also used in the treatment of skin disorders and irritations, such as eczema, dandruff, folliculitis, warts, *pityriasis versicolor*, psoriasis and acne. It has natural antiseptic properties and plays an essential role in the synthesis of collagen. Well-designed studies, most conducted in Israel, suggest that balneotherapy/sulfur can help treat several different kinds of arthritis. People who took sulfur baths and other spa therapies improved strength, had less morning stiffness, had better walking ability, and less inflammation, swelling, and pain in joints, particularly in the neck and back.

Homeopathic formulations in accordance of the present invention can include tinctures and/or dilutions of Sulfur. In some embodiments, a mother tincture of Sulfur can include about 1 to about 30 grams of Sulfur dissolved in about 30 to about 60 ml of water and/or alcohol. Various dilutions can be made from the mother tincture. Dilutions of Sulfur may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any Sulfur dilution, prior to, or after blending to form a homeopathic formulation. In some embodiments, homeopathic formations can be made from include Sulfur dilutions of 10C. In other embodiments, homeopathic formulations can be made from Sulfur dilutions of 30C. In yet other embodiments, homeopathic formulations can be made from Sulfur dilutions of 50M. In another embodiment, homeopathic formulations is a blended formulation including various Sulfur dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include Sulfur dilutions in an amount ranging from about 5% to about 40%, about 10% to about 20% relative to the total volume of the final formulation.

*Urtica*

*Urtica* has been used for hundreds of years to treat painful muscles and joints, eczema, arthritis and gout. Today it is also used to treat urinary problems during the early stages of benign prostatic hyperplasia, for urinary tract infections, for hay fever/allergic rhinitis (reduced sneezing and itching), or for treating joint pain, sprains and strains, tendonitis, and insect bites. Homeopathic formulations in accordance of the present invention can include tinctures and/or dilutions of *Urtica*. In some embodiments, a mother tincture of *Urtica* can include about 1 to about 30 grams of *Urtica* dissolved in about 30 to about 60 ml of water and/or alcohol. Various dilutions can be made from the mother tincture. Dilutions of *Urtica* may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any *Urtica* dilution, prior to, or after blending to form a homeopathic formulation. In some embodiments, homeopathic formations can be made from include *Urtica* dilutions of 10C. In other embodiments, homeopathic formulations can be made from *Urtica* dilutions of 30C. In yet other embodiments, homeopathic formulations can be made from *Urtica* dilutions of 50M. In another embodiment, homeopathic formulations is a blended formulation including various *Urtica* dilutions. Examples of such blended formulation, without limitation, includes blended formulation of 10C/30C/50M, 10C/100C/100M, 5C/30C/50M, 30C/100C/200M and 100C/200C/1000M. Homeopathic formulations may include *Urtica* dilutions in an amount ranging from about 5% to about 40%, about 10% to about 20% relative to the total volume of the final formulation.

Nosodes

Nosodes includes one or more infectious agents in minute doses in dilutions. Non limiting examples of Nosodes include various species of Methicillin-resistant *Staphylococcus aureus* (MRSA), microplasms, *Aspergillus niger, Candida, Mucor racemosus*; and infections agents that act to infect wounds, particularly burn wounds/injuries, that would include Gram-negative bacteria, and Gram-positive bacteria. Homeopathic formulations in accordance with the present invention can include tinctures and/or dilutions of Nosodes. In some embodiments, a mother tincture of Nosodes can include about 0.1 to about 5 grams of Nosodes dissolved in about 30 to about 60 ml of water and/or alcohol. Various dilutions can be made from the mother tincture. Dilutions of Nosodes may include X, C and M dilutions. X dilutions may range in potency from about mother tincture to about 500 X; about 2 X to about 300 X; about 5 X to about 100 X; about 5 X to about 50X. C dilutions may range in potency from mother tincture to about 500 C; about 2 C to about 300 C; about 5 C to about 100 C; about 5 C to about 50C. M dilutions may range in potency from about mother tincture to about 1000 M; about 2 M to about 300 M; about 5 M to about 200 M; about 5 M to about 100 M. Succussion can be performed on any Nosodes dilution, prior to, or after blending to form a homeopathic formulation. In some embodiments, homeopathic formations can be made from include Nosodes dilutions of 12C. In other embodiments, homeopathic formulations can be made from Nosodes dilutions of 30C. In yet other embodiments, homeopathic formulations can be made from Nosodes dilutions of 50M. In another embodiment, homeopathic formulations is a blended formulation including various Nosodes dilutions. Examples of such blended formulation, without limitation, includes blended formulation of 12C/30C/50M, 30C/100C/100M, 5C/30C/50M, 30C/100C/200M and 100C/200C/1000M. Homeopathic formulations may include Nosodes dilutions in an amount ranging from about 3% to about 40%, about 10% to about 20% relative to the total volume of the final formulation.

Formulation

The homeopathic formulation of the present invention comprises at least one dilution of *Arnica*, at least one dilution of *Calendula*, at least one dilution of *Echinacea*, at least one dilution of *Hypericum*, at least one dilution of Silver, at least one dilution of Sulfur, at least one dilution of *Thiosinaminum*, and at least one dilution of *Urtica*.

The homeopathic formulation of the present invention comprises at least one dilution of *Arnica*, at least one dilution of *Calendula*, at least one dilution of *Echinacea*, at least one dilution of *Hypericum*, at least one dilution of Silver, at least one dilution of Sulfur, at least one dilution of *Thiosinaminum*, and at least one dilution of *Urtica*. In some embodiments, the dilutions of *Arnica* is present in an amount ranging from about 5% to about 30%, preferably about 10% to about 20%; the dilutions of *Calendula* is present in an amount ranging from about 5% to about 30%, preferably about 10% to about 20%; the dilutions of *Echinacea* is present in an amount ranging from about 5% to about 30%, preferably about 10% to about 20%; the dilutions of *Hypericum* is present in an amount ranging from about 5% to about 30%, preferably about 10% to about 20%; the dilutions of Silver is present in an amount ranging from about 5% to about 30%, preferably about 5% to about 30%, preferably about 10% to about 20%; the dilutions of Sulfur is present in an amount ranging from about 5% to about 30%, preferably about 10% to about 20%; the dilutions of *Thiosinaminum* is present in an amount ranging from about 5% to about 30%, preferably about 10% to about 20%; and the dilutions of *Urtica* is present in an amount ranging from about 5% to about 30%, preferably about 10% to about 20% relative to the total volume of the formulation. The amount of the dilutions may be adjusted depending on the particular application.

In various embodiments of the formulation, the potency of the at least one dilution of *Arnica* ranges from mother tincture to about 1000 M; the potency of the at least one dilution of *Calendula* ranges from mother tincture to about 1000 M; the potency of the at least one dilution of *Echinacea* ranges from mother tincture to about 1000 M; the potency of the at least one dilution of *Hypericum* ranges from mother tincture to about 1000 M; the potency of the at least one dilution of Silver ranges from mother tincture to about 1000 M; the potency of the at least one dilution of Sulfur ranges from mother tincture to about 1000 M; the potency of the at least one dilution of *Thiosinaminum* ranges from mother tincture to about 1000 M; and the potency of the at least one dilution of *Urtica* ranges from mother tincture to about 1000 M. The potency of the dilutions may be adjusted depending on the particular application.

Solvent

Homeopathic formulations in accordance with the present invention include a solvent. Non limiting examples of the solvent include water, alcohol, oil, any other physiological fluid, and a mixture thereof. In some embodiments, homeopathic formulations may include a solvent ranging from about 0.075% to about 100% relative to the total weight of the formulation.

Inactive Ingredients

Homeopathic formulations in accordance with the present invention may further comprise one or more inactive ingredients, such as excipients that are common to the health and/or cosmetic industries, as well as minerals, such as sea minerals. Sea mineral, which can be included in the homeopathic formulation of the present invention include one or more of the following elements: Antimony, Barium, Beryllium, Bismuth, Boron, Bromine, Cadmium, Calcium, Carbonate, Cerium, Cesium, Chloride, Chromium, Cobalt, Copper, Dysprosium, Erbium, Europium, Gadolinium, Gallium, Germanium, Gold, Hafnium, Holmium, Indium, Iodine, Iridium, Iron, Lanthanum, Lead, Lithium, Lutetium, Magnesium, Manganese, Molybdenum, Neodymium, Nickel, Niobium, Osmium, Palladium, Phosphorus, Platinum, Potassium, Praseodymium, Rhenium, Rhodium, Rubidium, Ruthenium, Samarium, Scandium, Selenium, Silicon, Silver, Sodium, Strontium, Sulfate/Sulfur, Tantalum, Tellurium, Terbium, Thallium, Thorium, Thulium, Tin, Titanium, Tungsten, Vanadium, Ytterbium, Yttrium, Zinc, Zirconium, plus other naturally occurring trace minerals found in seawater.

Preservative, such as potassium sorbate, can also be included in the homeopathic formulations. The formulations can include anti-infection agents/antimicrobial agents that can also act to preserve, for example silver. Other medicament, such as opioid, can also be included in the homeopathic formulations. In a preferred embodiment, opioid is not included in the formulation.

The compositions herein taught might also be combined with surfactants and or items such as Dimethyl sulfoxide (DMSO) that may assist, such as, in the penetration of the skin. Other examples of some excipients used in accordance with the invention are viscosity modifying agents, buffers, antioxidants, emulsifying agents, absorbents, anti-acne agents, antiperspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, flavoring agents humectants, keratolytics, opacifying agents, pH adjusters, preservatives, propellants, proteins, retinoids, reducing agents, sequestrants, skin bleaching agents, skin-conditioning agents (humectants, miscellaneous, and occulsive), skin soothing agents, skin healing agents, softeners, solubilizing agents, lubricants, penetrants, plastisizers, solvents and co-solvents, sunscreening additives, sweeteners, salts, essential oils, and vitamins. In some embodiments, homeopathic formulations may include inactive ingredients ranging from about 0.01 wt % to about 95 wt % relative to the total weight of the formulation.

Mode of Delivery

The homeopathic formulations of the present invention can be prepared in various forms of preparation desired for administration. The homeopathic formulation can be formulated to be administered orally, parenterally, intravenously, intramuscularly, intrathecally, subcutaneously, sublingually, gingivally, buccally, rectally, vaginally, ocularly, nasally, by inhalation, cutaneously, topically, systematically, and transdermally. The homeopathic formulations can be formulated as liquids, spray, a drop, e.g., an eye drop, liquid in atomized form via, e.g., a nebulizer, and aerosolized inhaler, capsules, tables, capsules, gel capsules, powders, chewable tablets, dissolvable tablet/sheet, cream, gel, suppository, ring, gel, ointment, lotion, lozenge, (including frozen lozenge), and patch.

In an embodiment, the formulation of the present invention is used in liquid form, and preferably administered as a topical spray, wherein this spray would be applied directly onto an area/s of concern, which could be outside and/or inside the body. The use of this formulation within a topical spray for use on the outside the body, could for example be applied onto such areas such as skin, eyes, ears, joints, feet, hands, back, face, legs, arms, back and any parts of the body. The formulation can also be sprayed directly onto trunks/pathways, as found, for example, in neck and spinal area, and also nasal cavities, mouth and throat.

Method of Treatment

The homeopathic formulation of the present invention can be used to treat pain, aches and discomfort in general, and specifically pain associated with burn wounds including all types of 1st, 2nd, 3rd and 4th degree burns, chemical, scalding, and electrical burns. The homeopathic formulation of the present invention administered via topical spray is a multi-modality aid that provides eight synergistic benefits: (1) stops/relieves pain and discomfort; (2) fights/minimizes infection; (3) stimulates healing and epithelization; (4) reduces inflammation; (5) increases perfusion; (6) prevents/minimizes scar tissue; (7) moisturizes wound/skin and (8) reduces itching/puruitus. In a preferred embodiment, the homeopathic formulation of the present invention is non-toxic, non-addictive, opiate free, taste free, steroid free, non-greasy, safe, non-staining, scent free and hypoallergenic, and therefore can be applied generally as needed to the area of need liberally. In some embodiments, the formulation is effective in about 5 seconds to 20 minutes, preferably about 10 seconds to about 15 minutes.

Other non-limiting examples of the uses of homeopathic formulation of the present invention include treatment of general wounds, arthritis, lower back pain, acute and/or chronic pain, sinus, hay fever, allergies frostbite, sore/red eyes, rashes, mouth sores, pressure ulcers, neuropathic pain, incisions, and wounds that include burn wounds, muscle spasms/sprains, cuts, lacerations, abrasions, surgical incisions, joint pain; insect bites and stings; bruised or injured sore aching areas, repetitive use pain, e.g., carpal tunnel syndrome, abrasions, surgical cuts, lesions, blisters, rubbed, chafed areas, crotch rot, jungle rot, plant induced inflammation rashes, trigeminal pain, tooth pain/discomfort; gum pain/discomfort, inflamed eyes, sore/inflamed throat, odor abatement, e.g., odor abatement associated with mouth (halitosis/bad breath), wounds, bandage/s, underarm, vagina, menstrual pads/inserts, feet. cancer/cancerous tumors for stasis/remediation/pain, for moisturization of skin, scar tissue minimization, to treat inflammation, to stop itching; to stimulate the body's healing response; for antimicrobial enhancement, to treat irritable bowel syndrome. The primary treatment of the condition using the present invention could provide the secondary benefit including, but not limited to sleep enhancement, stress/anxiety/depression relief, and cancer/cancerous tumors stasis/remediation (such as by increasing immune system function and enhancing cellular transduction/signaling). The formulation of the present invention may also be applied to fruits and vegetables to delay spoilage due to decreased bacterial/enzymatic action.

EXAMPLES

The following are the some examples of the formulation in accordance with the present invention.

Example 1

A blended dilution can be made as illustrated below in Table 4:

TABLE 4

| Active Ingredients | Potency | Volume (ounces) | v/v % |
|---|---|---|---|
| Arnica | 10C | 2 | 3.7 |
| Arnica | 30C | 2 | 3.7 |
| Arnica | 50M | 2 | 3.7 |
| Calendula | 10C | 2 | 3.7 |
| Calendula | 30C | 2 | 3.7 |
| Calendula | 50M | 2 | 3.7 |
| Echinacea ANG | 10C | 2 | 3.7 |
| Echinacea ANG | 30C | 2 | 3.7 |
| Echinacea ANG | 50M | 2 | 3.7 |
| Hypericum | 10C | 2 | 3.7 |
| Hypericum | 30C | 2 | 3.7 |
| Hypericum | 50M | 2 | 3.7 |
| Silver | 10C | 2 | 3.7 |
| Silver | 30C | 2 | 3.7 |
| Silver | 50M | 2 | 3.7 |
| Sulfur | 10C | 2 | 3.7 |
| Sulfur | 30C | 2 | 3.7 |
| Sulfur | 50M | 2 | 3.7 |
| Thiosinaminum | 10C | 2 | 3.7 |
| Thiosinaminum | 30C | 2 | 3.7 |
| Thiosinaminum | 50M | 2 | 3.7 |
| Urtica | 10C | 2 | 3.7 |
| Urtica | 30C | 2 | 3.7 |
| Urtica | 50M | 2 | 3.7 |
| Nosode: Methicillin-resistant Staphylococcus aureus | 50M | 2 | 3.7 |
| Nosode: Pseudomonas areuginosa | 50M | 2 | 3.7 |
| TOTAL | | 54 | 100 |

Example 2

A blended dilution can be made as illustrated below in Table 5:

TABLE 5

| Active Ingredients | Potency | Volume (ounces) | v/v % |
|---|---|---|---|
| Arnica | 10C | 2 | 4.1666 |
| Arnica | 30C | 2 | 4.1666 |
| Arnica | 50M | 2 | 4.1666 |
| Calendula | 10C | 2 | 4.1666 |
| Calendula | 30C | 2 | 4.1666 |
| Calendula | 50M | 2 | 4.1666 |
| Echinacea ANG | 10C | 2 | 4.1666 |
| Echinacea ANG | 30C | 2 | 4.1666 |
| Echinacea ANG | 50M | 2 | 4.1666 |
| Hypericum | 10C | 2 | 4.1666 |

TABLE 5-continued

| Active Ingredients | Potency | Volume (ounces) | v/v % |
|---|---|---|---|
| Hypericum | 30C | 2 | 4.1666 |
| Hypericum | 50M | 2 | 4.1666 |
| Silver | 10C | 2 | 4.1666 |
| Silver | 30C | 2 | 4.1666 |
| Silver | 50M | 2 | 4.1666 |
| Sulfur | 10C | 2 | 4.1666 |
| Sulfur | 30C | 2 | 4.1666 |
| Sulfur | 50M | 2 | 4.1666 |
| Thiosinaminum | 10C | 2 | 4.1666 |
| Thiosinaminum | 30C | 2 | 4.1666 |
| Thiosinaminum | 50M | 2 | 4.1666 |
| Urtica | 10C | 2 | 4.1666 |
| Urtica | 30C | 2 | 4.1666 |
| Urtica | 50M | 2 | 4.1666 |
| TOTAL | | 48 | 100 |

Example 3

A liquid spray can be formulated using the blended formulations of Example 1 and 2 as shown in Table 6 and 7 below:

TABLE 6

| Ingredients | Volume (ounces) | v/v % |
|---|---|---|
| Blended Formulation of Example 1 | 54.000 | 95.9863 |
| Water | 2.000 | 3.5550 |
| Sea Mineral | 0.250 | 0.4444 |
| Silver | 0.008 | 0.0142 |
| TOTAL | 56.258 | 100 |

TABLE 7

| Ingredients | Volume (ounces) | v/v % |
|---|---|---|
| Blended Formulation of Example 2 | 48.0000 | 95.5081 |
| Water | 2.0000 | 3.9795 |
| Sea Mineral | 0.2500 | 0.4974 |
| Silver | 0.0075 | 0.0149 |
| TOTAL | 50.2575 | 100 |

Example 4

Figure 2:
FIG. 2 is a photograph showing the results after the composition in accordance with the present invention was applied to the burn wounds on hand as shown in FIG. 1.

The formulations of the invention were used to treat pain associated with burn wounds. The formulation in accordance with the present invention was topically applied to the burn wounds on hand as illustrated in FIG. 1 each day for 21 days. Total pain relief was achieved after the first day. As shown in FIG. 2, no infection or scar tissue occurred.

Example 5

Two male burn doctors and an another male individual purposely initiated eight second hot-plate burns on the ring fingers of their right and left hands. The formulation of the present invention was topically applied by spraying at 0.15 ml/spray onto only one burned finger of each person 5 seconds after the fingers were burned, and afterwards every 4 hours. The other burned finger of each individual was only treated with a standard measure of care. Constant nagging pain was felt for days on all of the fingers only treated with a standard measure of care. At no time was there any pain experienced by each person on the finger to which the formulation of the present application was topically applied.

Example 6

Figure 3:
FIG. 3 is a photograph of Cellulitis on a leg of a male patient.
Figure 4:
FIG. 4 is a photograph of the results of the composition in accordance with the present invention was applied to the Cellulitis on the leg as shown in FIG. 3.

A male in his 70's with Cellulitis on his left leg, as illustrated in FIG. 3, was in severe pain. His leg was severely inflamed/infected and was also itching, and was in a negative progression; his leg was medically non-responsive, and his prognosis was quickly approaching amputation. After using the formulation in accordance with the present invention as an adjunct therapy, within two hours, he experienced no pain and started a positive health progression. He used the formulation four times a day and continued for nine days and FIG. 4 illustrates this patient's leg, saved from amputation, treated with the formulation in accordance with the present invention.

Example 7

A male patient who had received significant incisions/sutures was expected to have significant post-operative pain for 3 days. The formulation in accordance with the present invention was topically applied via spray to the incisions/sutures areas every 30 minutes. This patient subsequently experienced no post-operative pain.

Example 8

A female patient in her 60's suffering from trigeminal neuralgia experienced excruciating pain shooting across her face, into her eyes, and the electrically exploding in her head for months. Pharmaceutical drugs had no positive effect in treating her pain, which was so frequent and intense that it elicited suicidal thoughts. The physician treating this female patient recommended anti-depressants and the possibility of exploratory brain surgery. This female patient topically applied the formulation in accordance with the present invention twelve times to 20 times a day to her face. Within 30 days, the pain had become manageable and within 90 days, the pain was minimal.

Example 9

A female patient in her 50's had severe medically unresponsive chronic lower back pain, which developed into such severity that she could not work. Daily her minute by minute waiting for paroxysmal pain to envelop her body brought deep anxiety, despair and suicidal thoughts. Her physician suggested anti-depressants and a hip replacement. The patient started the topical spray application of the formulation in accordance with the present invention by spraying 10 to 15 times a day. After 30 days, the explosive and overwhelming back pain dramatically diminished and she returned to work within 45 days.

Example 10

A male patient with severe asthma applied the formulation of the present invention to his forehead and upper chest area. Within 2-3, his breathing returned to normal and a feeling of balance and relaxation followed application of the formulation.

Example 11

A female had frequent pain in her right wrist area, apparently from the repetition from the many years that her work demanded as a hairstylist. After one topical spray application of the formulation in accordance with the invention, this female had a complete cessation of her wrist pain within 5 seconds.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating pain comprising administering to a patient in need thereof orally, sublingually, gingivally, buccally, rectally, ocularly, nasally, by inhalation topically, or transdermally a composition comprising therapeutically effective amounts of each of the following dilutions—at least one dilution of *Arnica*, at least one dilution of *Calendula*, at least one dilution of *Echinacea*, at least one dilution of *Hypericum*, at least one dilution of Silver, at least one dilution of Sulfur, at least one dilution of *Thiosinaminum*, and at least one dilution of Urtica, wherein each of said at least one dilutions has a potency of at least 10C to the potency of a mother tincture.

2. The method of claim 1, wherein the composition is formulated as a topical spray and wherein the topical spray is sprayed directly onto an area of concern on the outside of or inside the patient's body.

3. The method of claim 2, wherein the topical spray is applied to the patient's skin, eyes, ears, joints, feet, hands, back, face, neck, spinal area, legs, arms, back, nasal cavities, mouth or throat.

4. The method of claim 1, wherein the pain is associated with one or more burn wounds.

* * * * *